United States Patent [19]
Willits et al.

[11] Patent Number: 5,376,005
[45] Date of Patent: Dec. 27, 1994

[54] PARTIAL DENTURE WITH S-SHAPED JOINT

[75] Inventors: William G. Willits; Thomas P. Schmitt, Jr., both of Norfolk, Va.

[73] Assignee: Lab One Enterprises, L.C., Norfolk, Va.

[21] Appl. No.: 205,569

[22] Filed: Mar. 4, 1994

[51] Int. Cl.$^5$ ............................................ A61C 13/225
[52] U.S. Cl. ..................................... 433/177; 433/172
[58] Field of Search ............... 433/167, 170, 190, 177, 433/178, 172

[56] References Cited

U.S. PATENT DOCUMENTS 4,514,173  4/1985  Re ................................. 433/178
4,764,115  8/1988  Willits et al. .................. 433/177

Primary Examiner—Cary E. O'Connor
Attorney, Agent, or Firm—Rhodes, Coats & Bennett

[57] ABSTRACT

The present invention relates to a partial denture that includes a series of artificial teeth along with an opening formed on a ridge portion of the denture for allowing existing teeth to extend therethrough. In a preferred embodiment the partial denture is basically comprised of a relatively hard acrylic material. Around the opening formed in the ridge there is provided a relatively soft material and this includes an elastic strip that is formed in the partial denture adjacent the opening formed in the ridge for existing teeth. The elastic strip is molded adjacent the ridge opening and is particularly integrally molded with the relatively hard acrylic material that forms a substantial part of the partial denture. To assure a secure connection between the elastic retainer strip and the relatively hard acrylic material, there is provided a generally curved S-shaped molded joint between each end of the elastic retainer strip and the relatively hard acrylic material.

7 Claims, 2 Drawing Sheets

PARTIAL DENTURE WITH S-SHAPED JOINT

FIELD OF THE INVENTION

The present invention relates to dentures, and more particularly to a partial denture that includes an opening for accommodating existing teeth.

BACKGROUND OF THE INVENTION

Partial dentures are in wide use throughout the U.S. and the world. Partial dentures are especially popular because they give patients the option of keeping existing teeth while extracting those teeth that cannot for one reason or another be saved. This is particularly beneficial because dentists can encourage their patients to maintain existing teeth as long as practical. Because partial dentures are not unreasonably expensive, patients can from time-to-time have certain existing teeth extracted and new partial dentures constructed.

An example of a successful partial denture design that is very unique is found in U.S. Pat. No. 4,764,115. This partial denture is basically constructed of a relatively hard acrylic material Supported on the hard acrylic material is a series of artificial. teeth. However, the partial denture disclosed in this patent includes an opening formed in the ridge of the denture to accommodate two or more existing teeth. Formed around the opening in the ridge is a relatively soft material that in fact includes an elastic retainer strap that extends about the buccal flange area of the denture adjacent the opening formed in the ridge. The elastic: retainer strip is integrally molded with the relatively hard acrylic material. In use, the elastic retainer engages the gum area of the patient around the teeth and securely holds the partial. denture within the mouth of the patient. While this type of partial denture has been very successful and widely used, there have been cases where applied stress and force cause the elastic retainer strip to be pulled and separated from the relatively hard acrylic material. In those cases, the partial denture had to be repaired or replaced.

SUMMARY AND OBJECTS OF THE INVENTION

The present invention entails a partial denture of the type disclosed in U.S. Pat. No. 4,764,115. The partial denture that forms the present invention includes an improved generally S-shaped molded joint formed in the buccal flange between each end of the elastic retainer strip and the relatively hard acrylic material. The curved generally S-shaped molded joint forms a firm and secure connection between the elastic retainer strip and the relatively hard acrylic material and prohibits the retainer strip from becoming separated from the partial denture because of ordinary use.

It is therefore an object of the present invention to provide a partial denture of the type having an elastic retainer strip disposed adjacent an opening for existing teeth wherein there is provided a molded curved S-shaped joint between the opposite ends of the elastic retainer strip and the denture proper, whereby the curved shaped molded joint securely attaches the elastic retainer strip to the partial denture.

Another object of the present invention is to provide a partial denture of the character referred to above where the same includes an elastic retainer strip that is securely molded and secured within the partial denture, Other objects and advantages of the present invention will become apparent and obvious from a study of the following description and the accompanying drawings which are merely illustrative of such invention,

DETAILED DESCRIPTION OF THE INVENTION

Figure 1:
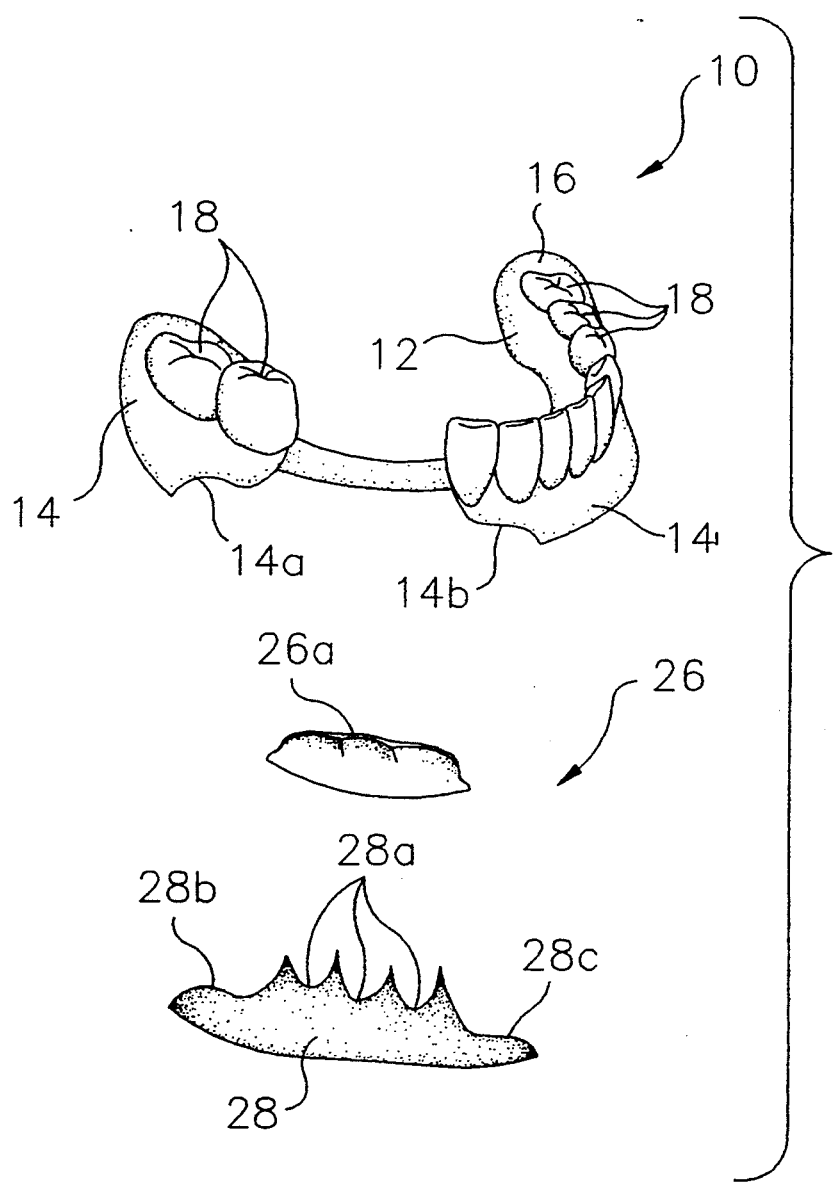
FIG. 1 is a perspective view of the partial denture with portions of the denture being broken away to better illustrate the structure as a whole.

With further reference to the drawings, the partial denture of the present invention is shown therein and indicated generally by the numeral 10. Viewing partial denture 10 in detail, it is seen that the same basically comprises a base or denture proper that conforms to a generally horseshoe shape. The base of the partial denture includes a rear lingual flange 12 and a front buccal flange 14. Buccal flange 14 and lingual flange 12 curve upwardly at the top to form a ridge 16. Selected artificial teeth 18 are mounted on the ridge 16.

The base or denture proper forms a generally inverted U-shaped gum cavity. This permits the entire partial denture 10 to be seated on the patient's gums.

Formed in the ridge 16 of the partial denture 10 is an elongated tooth opening 22. Opening 22 is designed to allow at least two existing teeth 24 to extend upwardly therethrough.

The basic structure of the partial denture 10 comprises a relatively hard acrylic material. This relatively hard acrylic material forms the buccal flange 14, lingual flange 12, and the ridge portion 16 of the partial denture.

Surrounding opening 22 is a relatively soft acrylic material that is indicated generally by the numeral 26. More particularly, the soft acrylic material 26 forms a soft acrylic edging 26a of the lingual side of the opening 22. This soft acrylic material 26 also includes an elastic retainer strip 28 that extends in front DE the existing teeth 24. In particular, the elastic retainer strip 28 engages the front gum area of the patient just underneath the existing teeth 24 as shown in the drawings. The top edge of the elastic retainer strip 28 includes a series of scalloped indentions 28a that tend to surround the base of the existing teeth 24 where the teeth join the top of the patient gum area. The soft acrylic material 26 including the elastic retainer strip 28 is integrally molded with the relatively hard acrylic material that forms a substantial part of the partial denture 10.

In constructing the partial denture 10 of the present invention, a full partial denture is usually constructed of the relatively hard acrylic material. Thereafter, the opening 22 is selectively cut in the ridge 16 so as to align with selected existing teeth 24. As a practical matter, in a preferred design, the partial denture 10 of the present invention is customarily used in conjunction with at least two side-by-side existing teeth. Therefore, the opening 22 is usually cut to accommodate two or more excessive existing teeth 24. Once opening 22 has been cut in the ridge 16, then a run or segment of the buccal flange 14 is cut from the partial denture 10. This creates a voided area in the buccal flange 14 that extends underneath the opening 22 and basically extends from one end of the opening to the other end, as seen in FIG. 1. There is also a voided area formed in the denture 10 on the lingual side of the existing teeth opening 22. Therefore, it is appreciated that the partial denture that one begins with during the construction process is cut and voided on both sides of the existing teeth opening 22. It will be appreciated from subsequent portions of this disclosure that these voided areas will be filled (except for the existing teeth opening 22) with the relatively soft acrylic material 26.

As seen in FIG. 1, when the voided area is removed from the buccal flange 14, there is left two terminal edges 14a and 14b that lie in spaced apart relationship. To accommodate a specific joint structure, the terminal edges 14a and 14b of the buccal flange 14 are particularly shaped. In the case of the present invention, terminal edges 14a and 14b are shaped into a generally curved S-shape as shown in the drawings.

Figure 2:
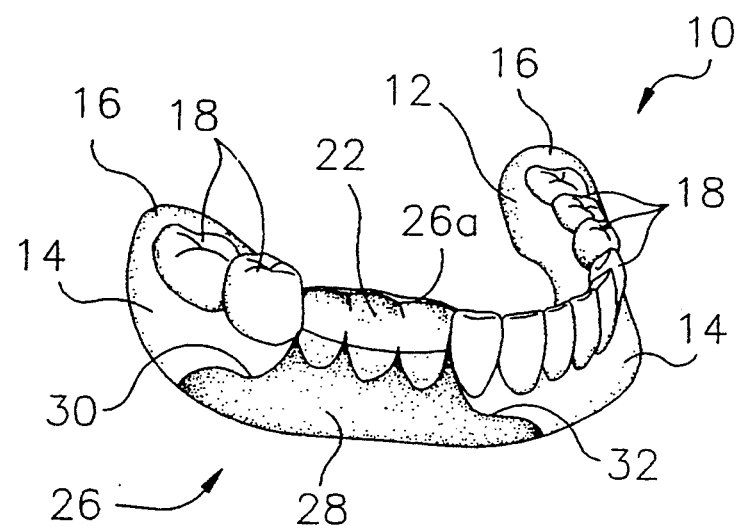
FIG. 2 is a perspective view of the partial denture of the present invention without the patient's existing teeth.
Figure 3:
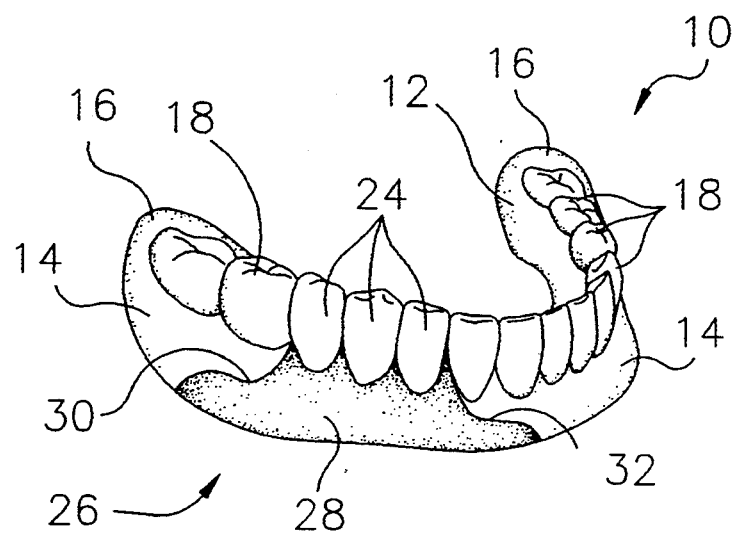
FIG. 3 is a perspective view of the partial denture showing the same having the patient's existing teeth projecting through a portion of the denture.

Once opening 22 has been formed and the void created in the buccal flange 14 adjacent the opening 22, then the relatively soft acrylic material 26 is molded to the base or denture proper of the partial denture 10. As pointed out above, a soft acrylic edging or strip 26a is molded around the lingual side of the opening 22. This soft acrylic edging or strip 26a is molded into the relatively hard acrylic material. Also, the elastic retainer strip 28 forms a part of the relatively soft acrylic material 26 that surrounds the tooth opening 22. In the case of the elastic retainer strip 28, the strip itself includes opposed terminal ends 28b and 28c. Terminal ends 28b and 28c are cut or shaped to conform with the curved or S-shaped terminal edges 14a and 14b of the buccal flange 14. Thus, when the elastic retainer strip 28 is actually molded into the relatively hard acrylic material there is formed two curved shaped molded joints 30 and 32 between the relatively hard acrylic material and the opposed ends 28b and 28c of the elastic retainer strip 28. Note from the drawings, particularly FIGS. 2 and 3, that the curved molded joints 30 and 32 are inclined inasmuch as each joint runs from an upper area adjacent one opposed end of the opening 22 downwardly and outwardly towards the bottom portion of the partial denture 10. Thus, it is appreciated that the elastic retainer strip 28 is wider at its bottom than at its top. The curved shaped molded joints 30 and 32 provide greater surface contact between the relatively hard acrylic material and the opposed ends of the elastic retainer strip 28.

From the foregoing specification and discussion, it is seen that the present invention presents a new and unique partial denture that includes an elastic retaining strip 28 integrally molded into the front buccal flange 14 of the denture. The curved or S-shaped molded joints 30 and 32 formed in the denture and particularly joining the opposite ends of the elastic retaining strip 28 with the base of the denture securely joins the elastic retaining strip 28 and generally prohibits premature failure due to stress or forces that act against the elastic retainer strip 28 and cause the same to be pulled from the base of the partial denture.

The present invention may, of course, be carried out in other specific ways than those herein set forth without parting from the spirit and essential characteristics of the invention. The presently embodiments are, therefore, to be considered in all respects as illustrative and not restrictive, and all changes coming within the meaning and equivalency range of the appended claims are intended to be embraced therein.

What is claimed is:

1. A partial denture comprising:
    a) a denture base including buccal and lingual flanges molded of a relatively hard acrylic material and shaped to form a ridge for supporting a selected number of artificial teeth;
    b) an opening formed in the ridge with the opening being at least large enough to receive a plurality of existing teeth;
    c) a voided area formed in the relatively hard acrylic material and in the buccal flange adjacent the elongated tooth opening;
    d) a pair of laterally spaced S-shaped terminal edges formed on opposite sides of the voided area in the relatively hard material in the buccal flange;
    e) an elastic material surrounding the opening for receiving the existing teeth and including an elastic strip that extends through the voided area between the S-shaped terminal edges of the relatively hard material of the buccal flange;
    f) the elastic strip including a pair of opposed S-shaped terminal ends that match with the S-shaped terminal edges formed in the relatively hard material of the buccal flange; and
    g) a pair of laterally spaced S-shaped molded joints formed in the buccal flange of the denture between the S-shaped terminal edges of the relatively hard material and the S-shaped terminal ends of the elastic strip so as to securely tie the elastic strip to the relatively hard acrylic material and to form a pair of laterally spaced S-shaped molded joints therein.

2. The partial denture of claim 1 wherein both S-shaped joints are disposed at an angle with respect to the existing teeth.

3. The partial denture of claim 1 wherein the molded S-shaped joints are disposed at an angle relative to a bottom plane of the partial denture.

4. The partial denture of claim 3 wherein the molded S-shaped joints extend generally downwardly and outwardly from the existing teeth opening formed in the ridge of the denture such that the base of the elastic strip tends to be wider than the top edge of the elastic strip that lies adjacent the opening in the ridge of the denture.

5. A method of forming a partial denture comprising the step of:
    a) forming a denture by molding a relatively hard acrylic material into a selected shape such that the formed denture includes both a buccal and lingual flange and an upper ridge;
    b) cutting an elongated opening in the ridge to form a teeth receiving opening;
    c) cutting a strip portion of the relatively hard acrylic material from the buccal flange in an area adjacent the opening formed in the ridge and thereby forming a pair of opposed terminal edges in the relatively hard acrylic material in the buccal flange;
    d) shaping the terminal edges of the relatively hard material into a generally curved S-shape;
    e) shaping opposite ends of an elastic strip such that each end assumes a generally curved S-shape and conforms generally to the shape of the terminal edges of the relatively hard acrylic material formed in the buccal flange; and f) molding the elastic strip between the terminal edges of the relatively hard acrylic material of the buccal flange and particularly forming a pair of molded generally curved S-shaped joints between the terminal edges of the relatively hard acrylic material of the buccal flange and respective generally S-shaped ends of the elastic strip so as to form a molded elastic strip below the opening for existing teeth such that the opening is bound along one side by the elastic strip that engages a gum area underlying the existing teeth and assists in retaining the partial denture about the gum area.

6. The method of claim 5 including the step of angling the generally curved S-shaped molded joints downwardly and outwardly, with respect to the bottom of the denture.

7. A partial denture comprising:
a) a denture base including buccal and lingual flanges molded of a relatively hard acrylic material and shaped to form a ridge for supporting a selected number of artificial teeth;
b) an existing tooth opening formed in the ridge:
c) a voided area formed in the relatively hard acrylic material and in the buccal flange adjacent the tooth opening;
d) a pair of laterally spaced curved and irregularly shaped terminal edges formed on opposite sides of the voided area in the relatively hard material in the buccal flange;
e) an elastic material surrounding the existing tooth opening including an elastic strip that extends through the voided area between the curved shaped terminal edges of the relatively hard material of the buccal flange;
f) the elastic strip including a pair of opposed curved and irregularly shaped terminal ends that match with the curved and irregularly shaped terminal edges formed in the relatively hard material of the buccal flange; and
g) a pair of laterally spaced curved and irregularly shaped molded joints formed in the buccal flange of the denture between the terminal edges of the relatively hard material and the terminal ends of the elastic strip so as to securely tie the elastic strip to the relatively hard acrylic material and to form a pair of laterally spaced curved and irregularly shaped molded joints therein.

* * * * *